Aug. 27, 1957 W. W. BUNGE Plant Pat. 1,637
ROSE PLANT
Filed Oct. 30, 1956
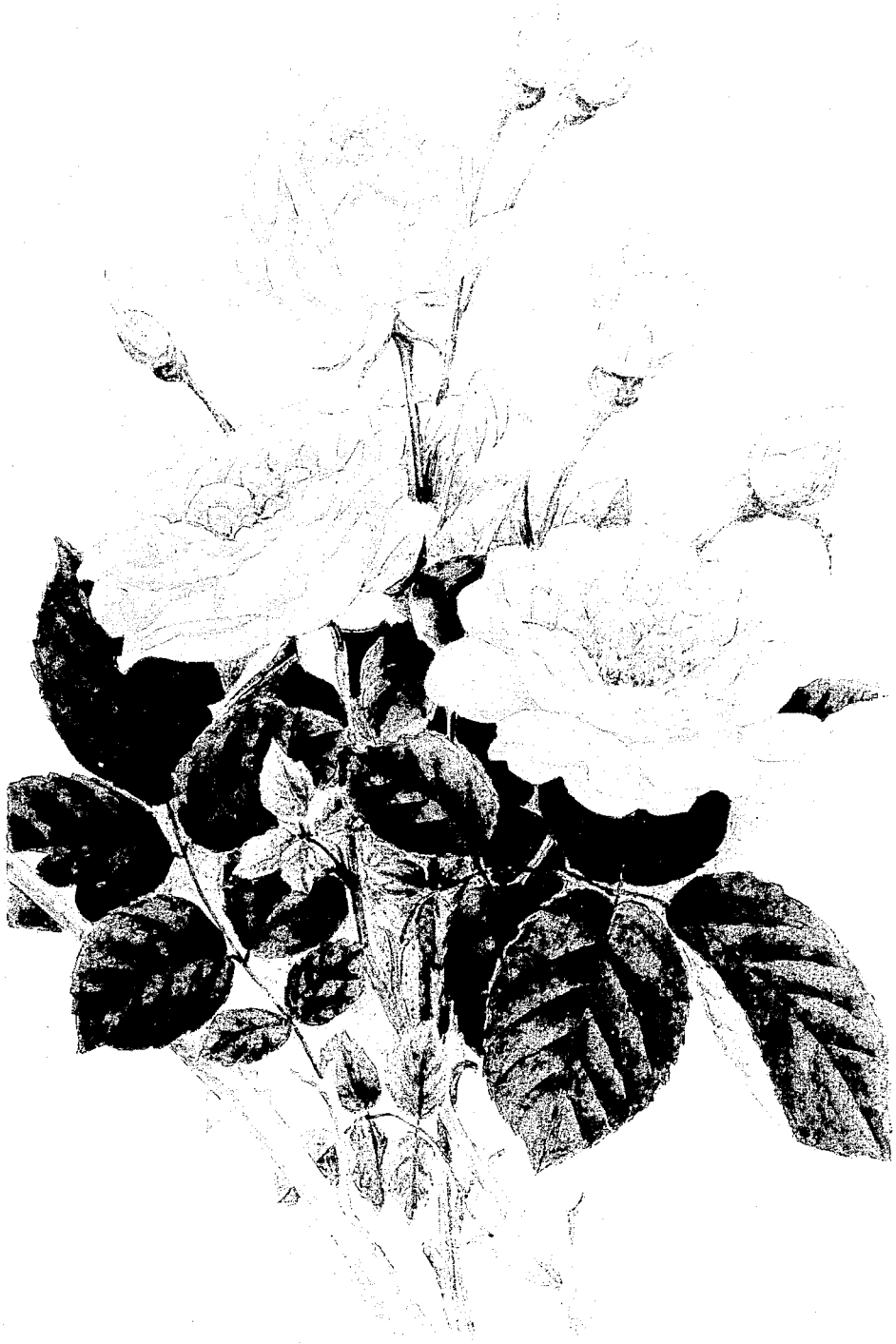
WITNESS
Addison E. Avery
INVENTOR
WALTER W. BUNGE
Hill, Sherman, Meroni, Gross & Simpson
ATTYS.

United States Patent Office

Plant Pat. 1,637
Patented Aug. 27, 1957

1,637

ROSE PLANT

Walter W. Bunge, Rochester, Minn.

Application October 30, 1956, Serial No. 619,371

1 Claim. (Cl. 47—61)

My invention relates to a new variety of rose plant.

My new variety of rose plant herein described illustrated in the drawing attached hereto and made a part hereof is a sport of the well known "Paul Neyron" rose (not patented). The buds of this sport bloom were asexually progagated in Rochester, Minnesota, by budding, have been re-budded numerous times and have come back to the original sport bloom, thereby perpetuating the novel characteristics in the progeny.

The parent plant for the plant of the instant invention was understood to be a "Paul Neyron" rose plant which was a bush-like plant, with spikes about three to four feet tall, the bush being about three feet wide, with pink colored blooms of moderately full size. In contrast, the instant sport blooms are noticeably larger in size and are several shades darker, having a purple-red color.

Also, my new variety of rose plant is much sturdier than the parent and it blooms earlier in the spring than the parent plant. My new rose plant also blooms again in July and August. The sturdy character of my plant is evidenced by its ability to survive the drastic weather conditions of Minnesota, and particularly the severe winters. My plant blooms as early as any hybrid tea rose or floribunda; and it has almost completed its spring blooming when the "Paul's Scarlet" (not patented) is starting.

My plant is a "pillar" rose rather than a "climber" in that it needs no support for the first six to eight feet. In addition, it differs from the parent plant in that it throws canes which grow in length from seven feet to as much as twelve feet. These canes shoot up from the bottom of the plant after blooming and the next year beautiful blooms develop thereon. I find that, if the seed knobs are cut off after the petals have fallen, then the canes shoot up as much as twelve feet in height. As these canes grow initially they have a reddish color which also appears in the leaves during the initial three feet of growth, but after this the leaves and the canes commence to lose their reddish tone and the leaves develop into the dark glossy green shown in the attached drawing. The tips of the canes retain a reddish cast.

The older canes at the bottom of the plant are from an inch to an inch and a half thick and are very strong and sturdy, being practically covered with large, heavy red thorns showing the hardiness of the plant in the northern climate. On the more recently developed canes which carry the blooms only a relatively few red colored thorns appear, as indicated in the attached drawing.

My rose plant is also unique in that it is an extremely healthy, hardy, vigorous growing pillar rose entirely suitable for the extremely severe climate of Minnesota and the fairly short growing season. For example, many of the new canes which shoot from the bottom of the plant after the first blooming grow as much as fourteen to sixteen inches a week which is better than two inches a day.

Although my rose plant grows better in the sun it has another distinct advantage in that I have grown beautiful plants in the shade. Such plants have been in the shade of a tree so that they are able to receive sunshine only a few hours of each day, but such plants grow well and are covered with beautiful blooms each year.

The blooms are of a dark, beautiful purple-red rose color, usually four or five inches in diameter. They are produced, either in a single bloom or in clusters up to as many as seven or eight in a cluser at the end of a vigorous stem from the main branch which may be eight to twenty-four inches long. The buds are not unusually long, but are large in circumference, and appear full and well shaped. This makes them particularly adaptable for cutting and arranging. The largest cluster which I have observed contained twenty-four beautiful blooms; and I have individual plants which have had from 200 to 300 blooms at one time.

The leaf growth is vigorous with dark green leaves having many serrations at the edges of the leaves. The vein distribution is extremely regular, branching off at the same intervals on each side of the middle vein. The deep dark healthy foliage is free from mildew and blackspot and also free from aphids. Over a period of time I have never found mildew or blackspot on my new plants, although I find that I must fight these diseases constantly with my other rose plants growing nearby.

The following is a detailed description of my new rose plant:

Parentage: Sport of "Paul Neyron."
Classification: Pillar.

*Flower*

Blooming habit: Early spring and then repeats in July and August.
Size of bloom: 4 to 5 inches in diameter and 2 inches in depth.
Form: Very compact high center area.
Petalage: 30 to 40.
Color: Purple red, slightly lighter on back of petal.
Texture: Thick and soft.
Fragrance: Delicate pleasant scent.
Stem: Light green with few reddish thorns.
Disease resistance: Extremely resistant to rose diseases including mildew and blackspot.
Bud:
*Size.*—1½ to 2 inches from base to tip.
*Form.*—Elongated and compact.
*Sepals.*—Fairly long, spatulated ends.
*Calyx.*—Hoods the bud.

*Genital organs*

Stamens-anthers: In mass of about ¾ inch in diameter.
*Color.*—Yellow.
*Arrangement.*—Massed around the pistils standing above the numerous red-tipped stigmas.
Styles: In mass.
Stigma: Has red tip.
Thorns: Only relatively few in the new portions of the plant; but in old portions near the base of the plant a very substantial number of sturdy thorns.

*Plant*

Form: Bush.

*Color*

The color designations according to "A Dictionary of Color by Maerz and Paul" are as follows:

Face of the petal—Purple Red—Plate 49–L–12.
Back of the petal—Purple Red—Plate 49–I–6.
Face of the leaf—Green—Plate 22–L–8.
Underside of the leaf—Green—Plate 20–E–6.

Having thus disclosed the invention I claim:

A new and useful variety of rose plant as herein shown and described, characterized particularly by its early blooming, repeat blooming in mid-summer, brilliant purple red color of blooms, extreme sturdiness and rapid growing rate under severe northern climatic conditions and resistance to rose diseases.

No references cited.